(12) United States Patent
Rios

(10) Patent No.: US 6,467,487 B1
(45) Date of Patent: Oct. 22, 2002

(54) HOLDING DEVICE FOR WRIST/SHOULDER ARTHROSCOPY AND SURGERY

(76) Inventor: Alberto Angel Rios, Riobamba 510, S. 41, F.99 Buenos Aires C1025ABK (AR)

( * ) Notice: Subject to any disclaimer, the term of this patent is extended or adjusted under 35 U.S.C. 154(b) by 0 days.

(21) Appl. No.: 09/853,871

(22) Filed: May 14, 2001

(51) Int. Cl.[7] .............................................. A61B 19/00
(52) U.S. Cl. ........................ 128/869; 128/878; 128/879; 602/32; 602/36
(58) Field of Search .............................. 602/32, 33, 35, 602/36, 38, 39, 40; 606/237, 240–242; 482/44, 47, 48; 128/845, 869, 878–879; 601/40; 269/71, 74, 95, 246, 60; 248/125.8, 159, 161, 354.3

(56) References Cited

U.S. PATENT DOCUMENTS

| | | | |
|---|---|---|---|
| 2,586,636 A | * 2/1952 | Fischer et al. ................. | 81/25 |
| 2,590,739 A | * 3/1952 | Wagner et al. ................. | 128/84 |
| 4,145,006 A | * 3/1979 | Webb ........................... | 269/69 |
| 4,445,506 A | * 5/1984 | Johansson et al. ............. | 602/39 |
| 4,969,636 A | * 11/1990 | Gautam ........................ | 269/71 |
| 6,012,456 A | * 1/2000 | Schuerch .................... | 128/869 |

* cited by examiner

Primary Examiner—Michael A. Brown
Assistant Examiner—Quang D Thanh

(57) ABSTRACT

A device for holding and immobilizing the hand of a patient for wrist and shoulder arthroscopy and/or surgery, the device comprising a threaded upright tower bar for moving up and down in an operating room table, and an horizontal arm for moving back and forth in an upper end of the upright bar, the horizontal arm having a proximal end for operation of the horizontal arm and a distal end for connecting to the patient's fingers.

10 Claims, 4 Drawing Sheets

HOLDING DEVICE FOR WRIST/SHOULDER ARTHROSCOPY AND SURGERY

BACKGROUND OF THE INVENTION

1. Field of the Invention

The present invention relates to the field of the arthroscopy and surgery of the wrist or shoulder of a patient and, preferably, the invention concerns a device for retaining or holding, or applying traction to, the hand and/or the arm of a patient for subjecting the same to arthroscopy and/or open surgery without the need of moving the patient. While only mention to arthroscopy and/or surgery of the wrist and shoulder is made in the present application, it will be obvious to any person skilled in the art that the principles of the present invention are applicable to the operation or treatment of any other limb of a patient, such as a foot/leg, which limb must be held in an position extended from the patients body during the operation.

2. Description of the Prior Art

It is well known that surgical operation imposes the surgeon and assistants to keep the patient stable and immobilized and this is of particular importance when a body member such a hand, foot, arm or leg is operated which operation requires precise and accurate operating movements in very small body rooms such as a wrist, shoulder, etc. For keeping the patient's member stable many devices, systems and structures are employed, all of them extremely cumbersome and bulky.

A device available at the marked through the firm Innomed Instrument Division under the trademark Medscape comprises a structure designed to fit onto an operating room table, the structure comprising four uprights bars capable of being fitted onto the O.R. table by means of socket clamps. The device also includes a tight assembly, a stabilizing bar and a tightening mechanism all operable to keep the structure stable and, hence, the patient's limb immobilized and stable. The volume occupied by this system is excessive and many components must be manipulated until setting the system for operation and during the operation thereof as well.

According to another system for operating the arm of a patient, the patient is placed in the O.R. table and the arm to be operated is connected to a traction suspension system having an arc portion connected to the O.R. table and a pulley arrangement fixed to the O.R. ceiling. Other systems for operating arms use an arrangement of several pulleys and ropes or slings with the pulleys being fixed to or suspended from the ceiling. This system not only is cumbersome and unsafety for the preparation, mounting and adjustment of all its components but also is bulky and the slings are an obstacle to the surgeon during the operation.

Another system particularly used for wrist arthroscopy and surgery combines a hand table forming part of the O.R. table with a vertical tower fixed to a base plate. The fingers of the patients are connected by means of straps to a cross piece that moves up and down along the vertical tower for the traction of the patient's forearm. While this system is simpler as compared to the above mentioned traction assemblies, the system is limited and restricted to basic and elemental movements and positioning.

There is a major drawback in all of the above traction or retention systems and this problem is related to the possibility that the surgeon, upon examining the situation once the member of the patient to be operated has been fixed to the traction device, decides to proceed with an operation that needs that the position of the patient's member be altered and place the member, a hand for example, firmly rested onto the operating table. To proceed with this action in all of the conventional devices, the hand must be left free and released from the device and the device repositioned with the prejudice of loosing sterilization of the device. It is important to remark that, while the device is sterilized entirely before entering the O.R. this sterilization is loosened in those parts of the device which are placed in contact with no sterilized parts of the operating table and equipment.

It would be therefore convenient to have a new system for holding, retaining and/or applying traction to a patient's limb, preferably a patient's arm, for operation purposes, with the possibility of positioning and stabilizing the arm in any desired position of a wide range of positions.

SUMMARY OF THE INVENTION

It is therefore one object of the present invention to provide a device for holding and immobilizing a limb of a patient for treating the same, preferably in surgery for the wrist or shoulder of a patient, the device comprising a telescopic upright tower bar for connecting to an operating room table and for moving up and down in the table, a horizontal arm connected to the upright bar for moving back and forth in the upright bar, the horizontal arm including a distal end for connecting to the patient's hand.

It is still another object of the present invention to provide a device for holding and immobilizing the hand/arm of a patient for surgery, the device comprising a base support for attaching to an auxiliary operating room table, an upright tower bar comprising an outer tubular bar having an outer threaded surface threadably connected to the base support and an inner threaded bore threadably receiving an inner threaded bar, the tubular bar having an upper end and a lower end and being movable up and down by rotating the bar in the base support, a horizontal arm threadably connected to an upper end of the inner bar, the horizontal arm having a proximal end for rotating the horizontal arm and moving the same back and forth, and a distal end for holding the fingers of the patient.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
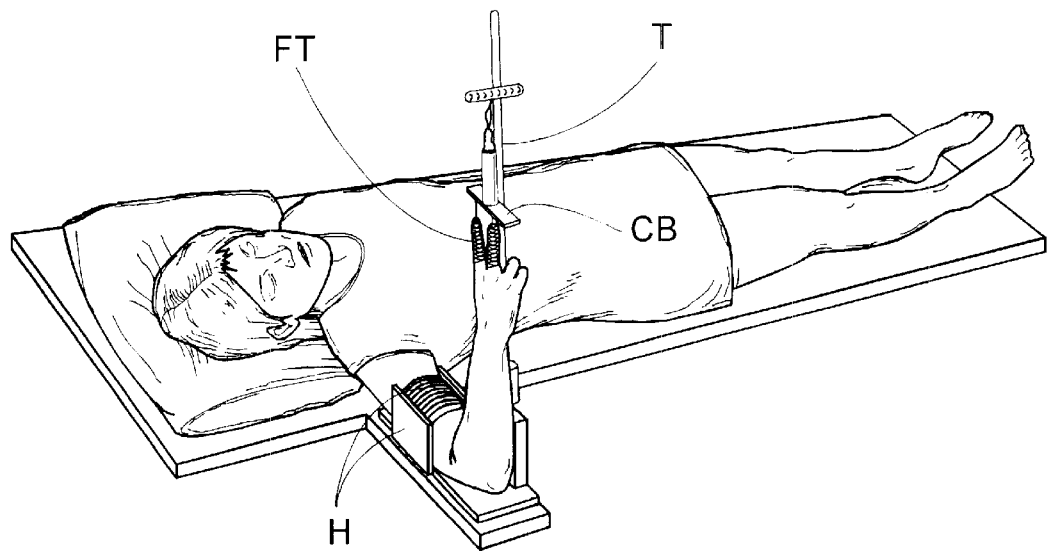
FIG. 1 shows a top perspective view of a patient in an operating room table with a patients hand held by a traction system using an upright bar with a pulling cross member, for wrist surgery, according to the prior art.

Now referring in detail to the drawings it may be seen from FIG. 1 a top perspective view of a patient placed in an operating room table and prepared for operation, with an arm holding system according to the prior art keeping the arm extended, wherein the fingers of the patient are retained in a typical mesh finger-trap FT which is connected to a cross bar CB which in turn is capable of being pulled along a tower T for applying traction to the patient's arm which is retained by a holder assembly H against the table.

Figure 2:
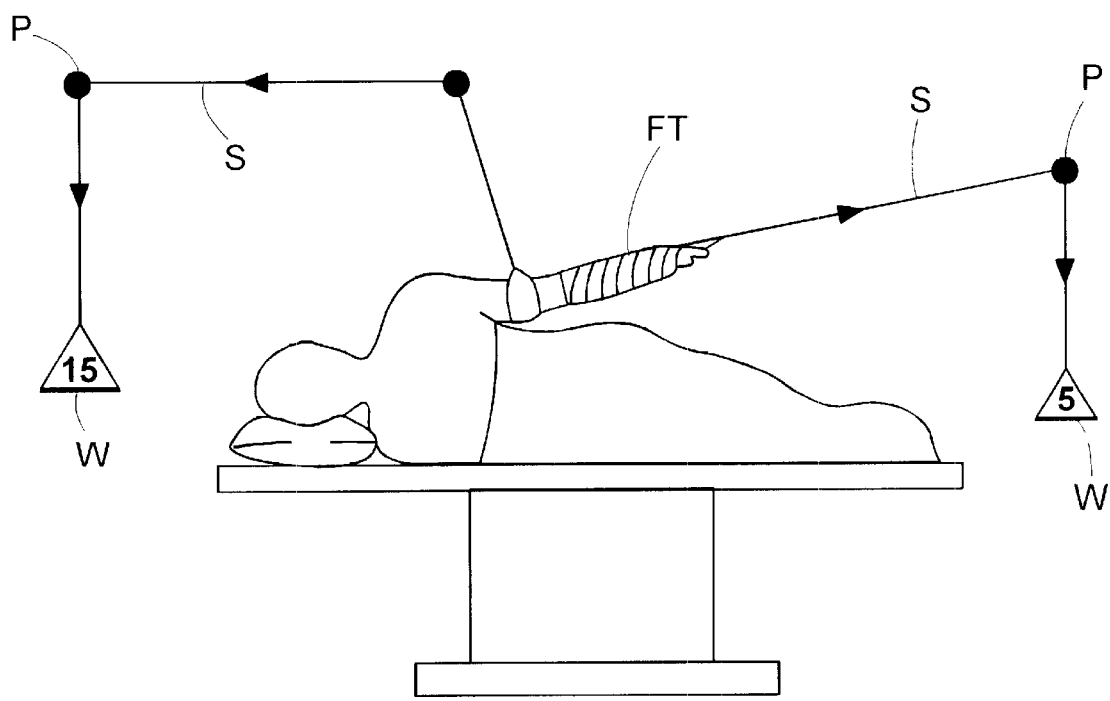
FIG. 2 shows a side diagrammatical view of a patient in an operating room table with a patient's arm held by a traction system using pulleys, slings and weights, for shoulder arthroscopy, according to the prior art.

FIG. 2 a side diagrammatical view of a patient placed in an operating room table and prepared for operation wherein the arm is extended by an arm holding system according to the prior art, wherein the arm of the patient is retained in a typical mesh trap FT, the arm being pulled by slings S passing onto pulley P and having weights W at the opposite end thereof. While only two sling/pulley systems are shown in FIG. 2, it is usual to employ a plurality of slings and pulleys which cause the system to be cumbersome for regulation and bulky for the surgeon operations. In addition to the foregoing, the possibilities of obtaining a variety of positions for the patient's arm is restricted to the number of the available pulleys and slings and the position thereof, however the much more elements involved the more cumbersome for its regulation and the less room available for the operation.

Since any of the above conventional devices have lost their sterility once connected to the operating table and/or ceiling it is obvious that any regulation thereof can not be performed by the surgeon who must keep his/her clothing sterilized. In addition, if the after carrying out an arthroscopy the surgeon decides to proceed with the operation of the patient's wrist or shoulder, all the traction system of the prior art must be disassembled and assembled again with the patient's wrist or shoulder repositioned. With these movements of the patient and the disassembling/assembling of the system the sterilization of the traction system is practically entirely lost.

Figure 3:
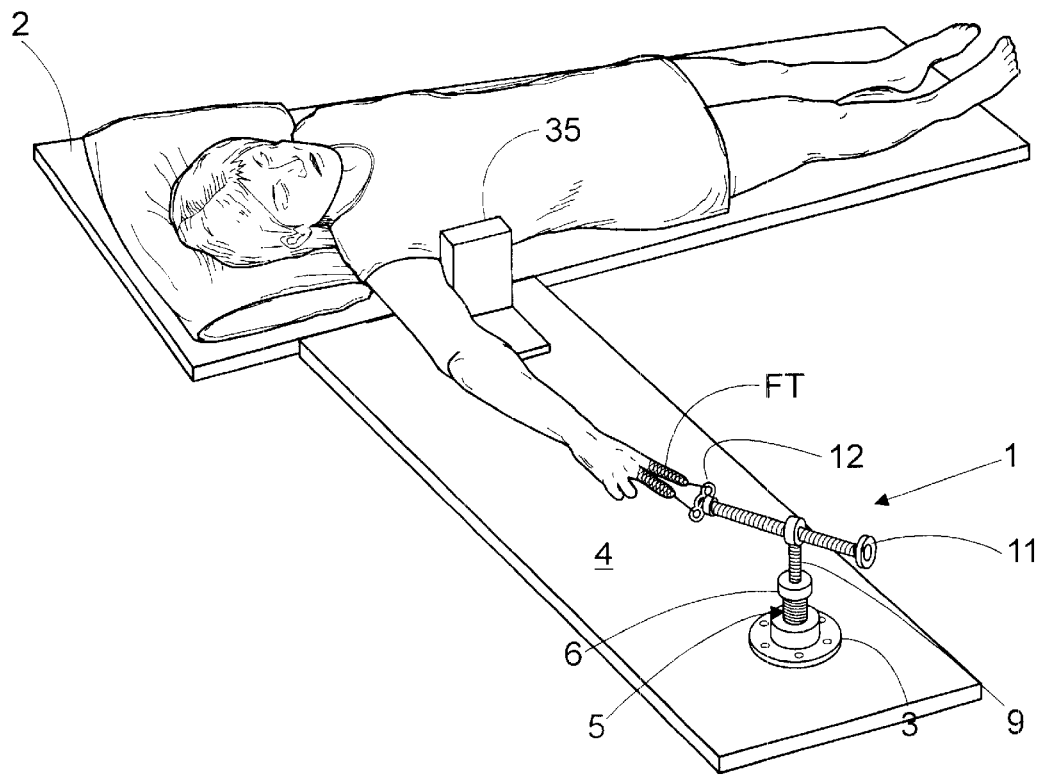
FIG. 3 shows a top perspective view of a patient in an operating room table with a patient's hand held by a system according to the present invention.

According to the invention, a device 1 for holding a patient's hand or arm is shown in FIG. 3, wherein the patient is placed onto an operating room table 2 with its fingers retained in conventional finger-traps which in turn are connected to the device of the invention. The inventive device comprises a base support 3 that may be fixed to the an auxiliary operating table 4 either permanently or temporarily whereby the table may be designed with the support already forming part of the table or the support may be removably attached to the table in which event, the device may be portable to be used in the physician office or in the room to make plasters. An upright tower bar is adjustably mounted onto the table through the base support, the upright tower comprising an outer tubular bar or tube 5 having an outer threaded surface threadably connected to base support 3, and the outer bar has an upper end 6, designed to be capable of being taken by the hand and rotate the tube, and a lower end 7. Tubular bar 5 is mounted in a way to be capable of moving up and down by rotating the bar in the base support. Bar 5 has a longitudinal threaded inner bore 8 receiving an inner threaded bar 9 that, in turn, moves up and down into bore 8 by rotation of bar 9 relative tubular bar 5.

Figure 4:
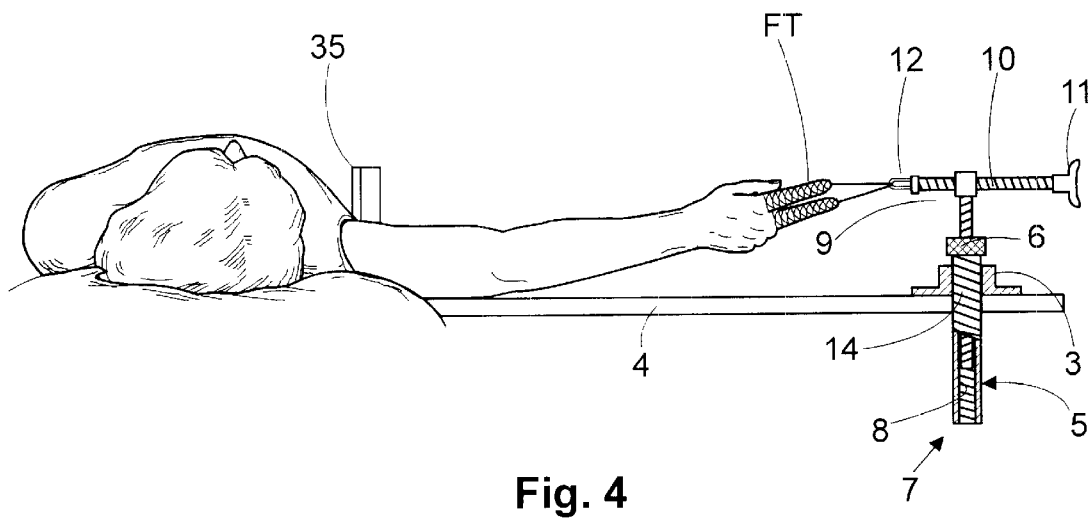
FIG. 4 shows an end side view of the patient and system of FIG. 3, also showing a partially cross-section of a mounting of the upright tower bar in a O.R. table, according to one embodiment of the invention.

Now making reference to FIG. 4, an embodiment of the arrangement for mounting tubular bar 5 in table 4 is shown, wherein base support 3 comprises a plate-like block fixed onto the auxiliary O.R. table by means of screws, the block having a threaded bore 14 for threadably receiving bar 5. Upper end 6 of bar 5 is for manually rotating the bar in order to move it up and down through support 3 with the purpose of adjusting the height of upper end 6 relative the table. Once the desired height of bar 5 is obtained the bar is firmly fixed in position. In this position, the tubular bar does not need to be moved again and any sterilized protector may be placed onto base 3 and the lower part of bar 5 in order to isolate these parts from the patient because these parts have lost their sterilization.

An horizontal arm 10 is threadably connected to an upper end 13 of the inner bar, and includes a proximal end 11 for rotating the horizontal arm and moving the same back and forth, and a distal end 12 for holding the fingers of the patient as it will be shown and described in detail with reference to other Figures.

Figure 5:
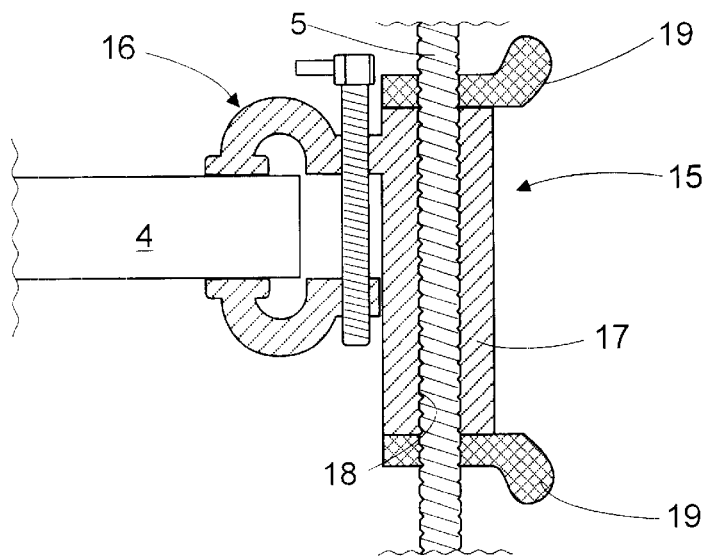
FIG. 5 shows a side elevational partially cross-sectional view of an alternative mounting of the upright tower bar in a O.R. table.

According to FIG. 5, another embodiment is shown wherein bar 5 is up and down movably mounted in the table by means of a base support 15 comprising a table socket clamp removably fixed to an edge of the operating room table, the socket clamp including a jaw retention portion 16 and a block 17 including a threaded bore 18 for threadably receiving tower bar 5. Like in the embodiment of FIGS. 3, 4, bar 5 can be moved, by rotation, up and down to adjust the height of end 6 relative to table 2 and the position may be fixed by wing nuts 19.

Figure 6:
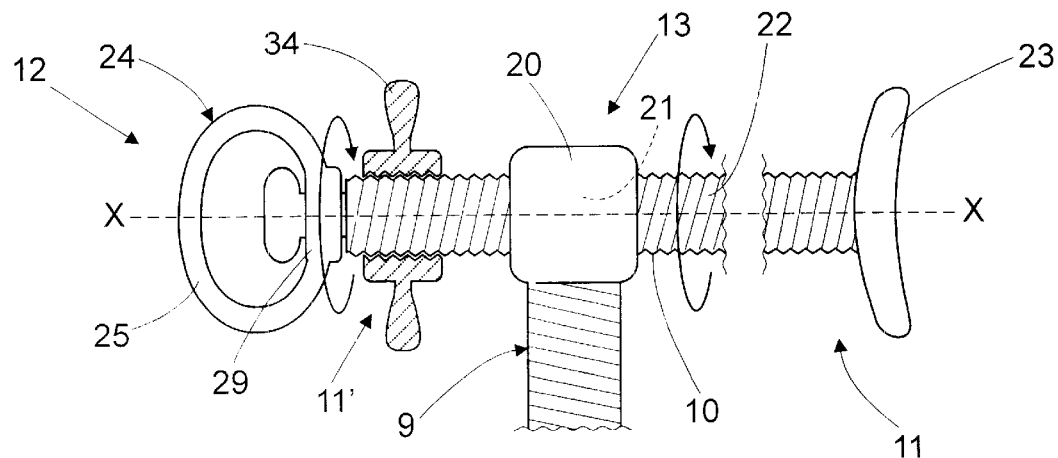
FIG. 6 shows a side elevational partially cross-sectional view of a mounting of the horizontal arm in the upright tower bar according to one embodiment of the invention.
Figure 7:
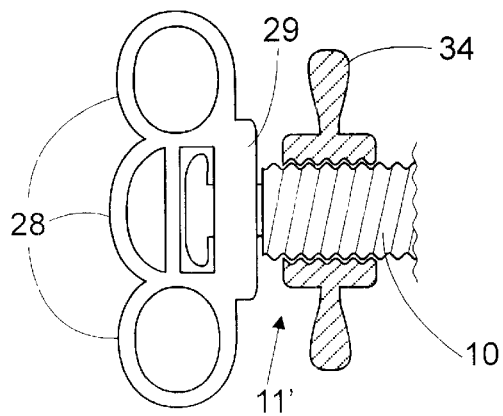
FIG. 7 shows a side elevational partially cross-sectional view of a finger holding member according to another embodiment of the invention.

As it is shown in FIG. 6, upper end 13 of inner bar 9 includes a sleeve 20 which is provided with a threaded bore 21 for threadably receiving horizontal arm 10 which also has an outer threaded surface 22. Arm 10 has at proximal end 11 thereof a wing handle 23 for manually rotating the horizontal arm in order to move it back and forth through sleeve 20. A distal end 11' of arm 10 is provided with a finger holding member 24 that preferably comprises one ring 25, as shown in FIG. 6, or a plurality of rings, three rings 26 for example, as shown in FIG. 7. In both embodiments, the ring or rings form part of a piece including a collar 29 that is freely rotatably mounted in distal end 11' of arm 10, to be capable of rotating in a longitudinal axis X—X of the horizontal arm. A fixing nut, for example a wing nut 34, is provided along arm 10 to fix finger holding member 24 in the desired position.

In operation, tubular bar 5 is rotated until the desired vertical position thereof is obtained and, if fixing nuts are provided, the same are adjusted at both insides, or at least at the upper side, of table 2. While the portion of bar 5 in contact with auxiliary table 2 has lost its sterility, inner bar 9 is still sterilized and is moved up and down within bar 5 until reaching the desired high and orientation of end 13. A protector (not shown) is placed around base support 3 to isolate these parts from the sterilized regions of the device and patient. Then, the patient's fingers are connected to ring 25 or rings 28 by finger traps well known in the art, and, once the traps are tied to the rings, horizontal arm 10 is rotated in order to move back to pull from the patient's fingers. Since a body support 35 is provided in the auxiliary table, the patient is prevented from being moved or pulled by the pulling force exerted by the traction device. Once the arm has reached the desired position, nut 34 is adjusted to fix member 24 also in the desired position in order to keep the patient's hand or arm stable and as immobilized as possible. If an arthroscopy is to be first carried out and the surgeon takes the decision of proceeding then with an operation, the patient does not need to be moved neither the device must be disassembled. The hand of the patient may be released from rings 24, 28 and placed onto the auxiliary operating table for operation purposes.

Figure 8:
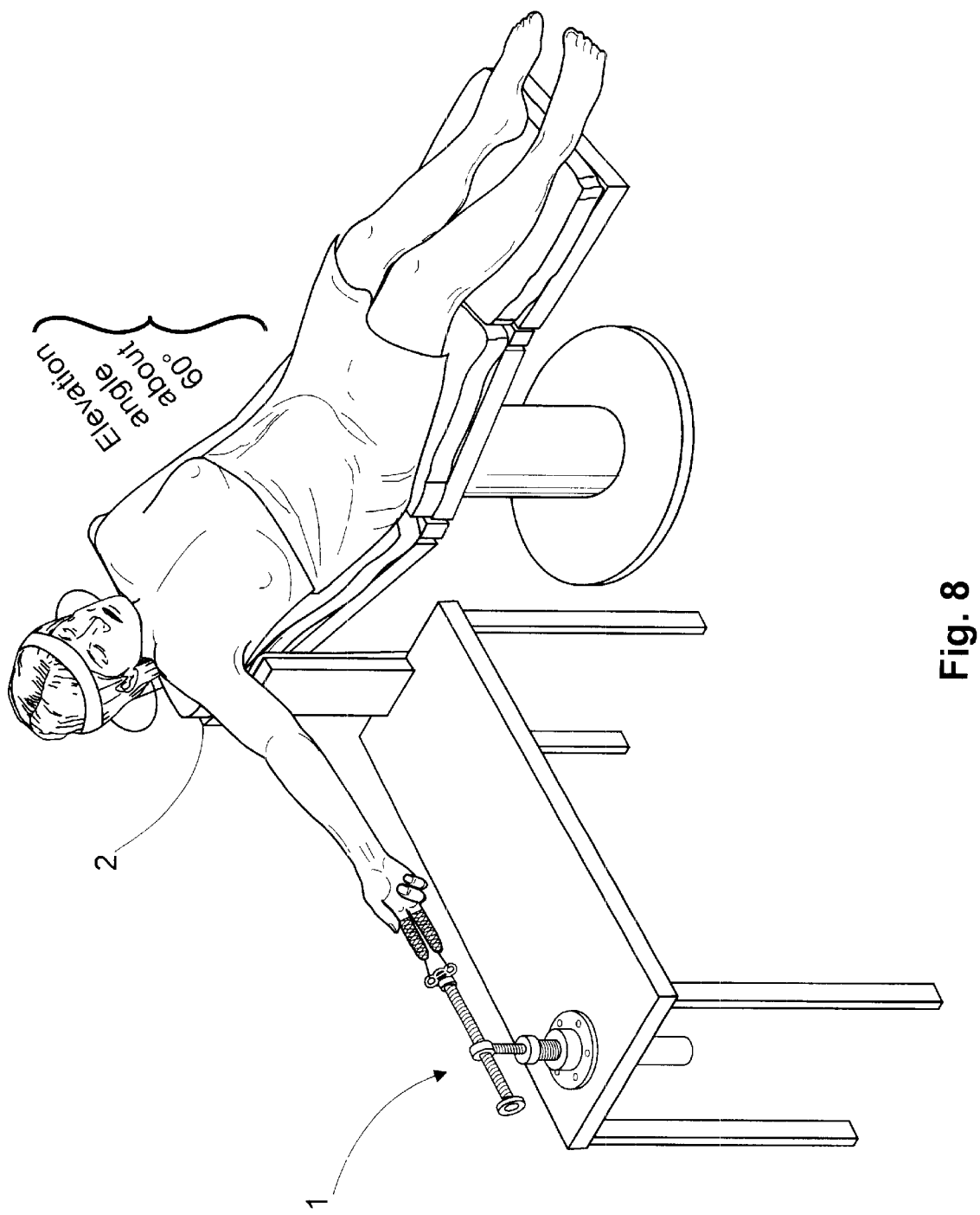
FIG. 8 shows an end elevational view of a patient in an operating room table with a patient's arm held by a traction system, for shoulder surgery, according to the invention.

According to another application of the inventive device in shoulder surgery, the patient is placed in a beach-chair position, as it is shown in FIG. 8, with the operating room table forming an angle of about 60° at the portion of the table for supporting the patient's back. The fingers of the patient will be taken to the inventive device in an appropriate manner, as illustrated, which permits to have the shoulder in a better position for open procedures as compared to the conventional position and system shown in FIG. 2. The patient, according to the invention, is placed onto the O.R. table with a sand bag SB for isolating the shoulder from no sterilized parts of the table. A stop or support 35 is also provided either in the O.R. table or in auxiliary table 4.

As it is clearly shown and described, the inventive device is simple for mounting and operating and provides for the surgeon and his/her assistants a clear and sufficient room to carry out all the necessary operating steps either in an arthroscopy or surgery or both. In addition, any necessary radioscopy can be carried out without the device being an obstacle to the radiation.

While preferred embodiments of the present invention have been illustrated and described, it will be obvious to those skilled in the art that various changes and modifications may be made therein without departing from the scope of the invention as defined in the appended claims.

I claim:

1. A device for holding and immobilizing the hand/arm of a patient for surgery, the device comprising:

a base support for attaching to an auxiliary operating room table, an upright tower bar comprising an outer tubular bar having an outer threaded surface threaded threadably connected to the base support and an inner threaded bore threadably receiving an inner threaded bar, the tubular bar having an upper end and a lower end and being movable up and down by rotating the bar in the base support, a horizontal arm threadably connected to an upper end of the inner bar, the horizontal arm having a proximal end for rotating the horizontal arm and moving the same back and forth, and a distal end for holding the fingers of the patient, wherein the upper end of the inner bar includes a sleeve mounted in said upper end, the sleeve including a threaded bore for receiving said horizontal arm.

2. The device of claim 1, wherein the base support comprises a block removably fixed to the auxiliary operating room table, the block including a threaded bore for receiving said tower bar.

3. The device of claim 1, wherein the base support comprises a table socket clamp removably fixed to the auxiliary operating room table, the block including a threaded bore for receiving said tower bar.

4. The device of claim 1, wherein the proximal end of the horizontal arm included a wing handle for manually rotating the horizontal arm.

5. The device of claim 1, wherein the distal end of the horizontal arm includes a finger holding member.

6. The device of claim 5, wherein the finger holding member comprises at least one ring.

7. The device of claim 6, wherein the finger holding member comprises a plurality of side-by-side arranged rings.

8. The device of claim 6, wherein at least one ring includes a collar freely rotatably mounted and retained in said distal end of the horizontal arm, whereby the ring can freely rotate in a longitudinal axis of the horizontal arm.

9. The device of claim 8, further comprising a wing nut in the horizontal arm for fixing the at least one ring in a desired position.

10. The device of claim 1, wherein the auxiliary table includes a body support for retaining the body of the patient against movement under a pulling force from the device.

* * * * *